(12) United States Patent
Shah

(10) Patent No.: US 7,883,667 B2
(45) Date of Patent: Feb. 8, 2011

(54) METHODS AND APPARATUS FOR EFFICIENTLY USING FLUIDS IN A SLIDE STAINER

(76) Inventor: Preyas Shah, 591 10th Ave., Warminster, PA (US) 18974

( * ) Notice: Subject to any disclaimer, the term of this patent is extended or adjusted under 35 U.S.C. 154(b) by 1114 days.

(21) Appl. No.: 11/062,045

(22) Filed: Feb. 18, 2005

(65) Prior Publication Data

US 2006/0188405 A1    Aug. 24, 2006

(51) Int. Cl.
*G01N 21/00*    (2006.01)
(52) U.S. Cl. .............................. 422/65; 422/63; 422/64; 422/66; 422/67; 422/99; 422/100; 436/180
(58) Field of Classification Search ............. 422/63–67, 422/99–100; 436/180
See application file for complete search history.

(56) References Cited

U.S. PATENT DOCUMENTS 4,241,017 A * 12/1980 Balistreri et al. .............. 422/58
4,435,063 A * 3/1984 Gunduz et al. .............. 396/602
4,738,824 A * 4/1988 Takeuchi ..................... 422/63
5,573,727 A   11/1996 Keefe
6,585,936 B1   7/2003 Shah
2002/0098118 A1 * 7/2002 Eckert et al. .................. 422/65

\* cited by examiner

*Primary Examiner*—Jyoti Nagpaul
(74) *Attorney, Agent, or Firm*—RatnerPrestia

(57) ABSTRACT

Apparatus and methods for applying fluid to slides are disclosed. The apparatus includes a partitioned vessel having a cavity and a sub-cavity that receives fluid, a slide carrier that receives at least one slide in an area corresponding to the sub-cavity, and a transport that positions the slide carrier to position the at least one slide at least partially within the sub-cavity of the partitioned vessel. Fluid is applied to the slides by partitioning the vessel to include a sub-cavity, filling the sub-cavity with fluid, and positioning the at least one slide into fluid filled sub-cavity.

11 Claims, 8 Drawing Sheets

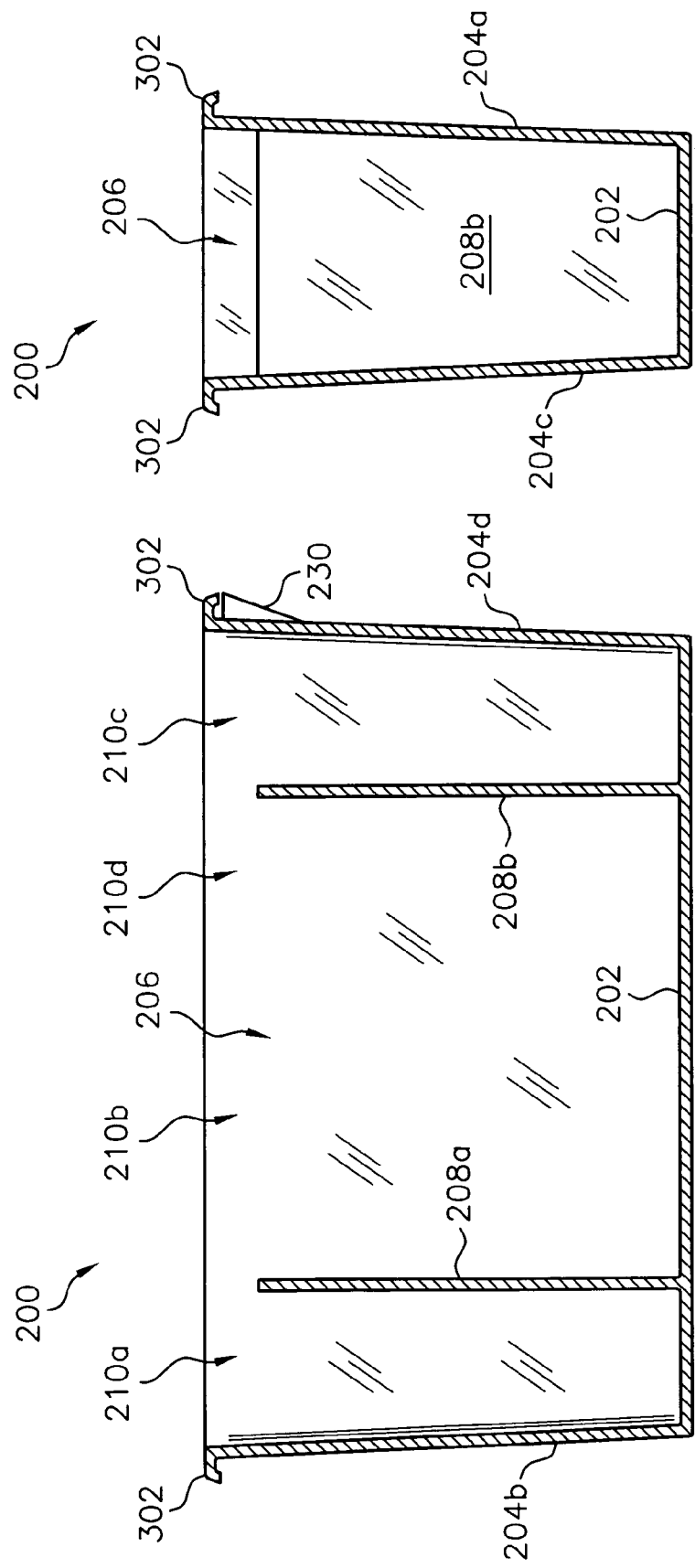

METHODS AND APPARATUS FOR EFFICIENTLY USING FLUIDS IN A SLIDE STAINER

FIELD OF THE INVENTION

The present invention relates to medical equipment and, more particularly, to methods and apparatus for efficiently using fluids in a slide stainer.

BACKGROUND OF THE INVENTION

Many medical tests are performed by examining a biological specimen, e.g., blood, pus, or urine, applied to a microscope slide. Typically, the biological specimen is "smeared" onto the slide and, then, treated with a reagent, such as a stain, to make features of the smeared biological specimen more visible. Often, the slide is then rinsed to remove excess reagent and dried for handling by laboratory personnel.

Automated slide stainers are available that automate the process of staining, rinsing, and drying smeared slides. One type of automated slide stainer is a dip and dunk slide stainer. In a dip and dunk slide stainer, one or more vessels are filled with reagents. The reagents are then applied to the slides by loading the slides into a slide carrier configured to accept up to a fixed number of slides (e.g., 40 slides) and selectively lowering the slide carrier containing the slides into the vessels, which are configured to accept the fixed number of slides.

Some of the reagents used for slide staining are very expensive and many cannot be reused, e.g., due to contamination. If the slide carrier is full (i.e., includes the fixed number of slides), then the price of the reagents is spread across a relatively large number of slides. If the slide carrier is not full, however, fewer slides are processed using the same amount of reagent. Thus, the reagents are less efficiently utilized when the slide carrier is not full, which results in a higher per slide processing cost.

There is an ever-present desire to reduce costs associated with laboratory processes such as slide-staining. Fluids such as reagents used in slide stainers contribute to the cost of slide staining processes. Accordingly, there is a need for slide staining methods and apparatus that more efficiently utilize these fluids. The present invention addresses this need among others.

SUMMARY

The present invention is embodied in methods and apparatus for applying a fluid to at least one slide. The apparatus includes a partitioned vessel having a cavity and a sub-cavity that receives fluid, a slide carrier that receives at least one slide in an area corresponding to the sub-cavity, and a transport that positions the slide carrier to position the at least one slide at least partially within the sub-cavity of the partitioned vessel. Fluid is applied to the slides by partitioning the vessel to include a sub-cavity, filling the sub-cavity with fluid, and positioning the at least one slide into fluid filled sub-cavity.

BRIEF DESCRIPTION OF THE DRAWINGS

The invention is best understood from the following detailed description when read in connection with the accompanying drawings, with like elements having the same reference numerals. When a plurality of similar elements are present, a single reference numeral may be assigned to the plurality of similar elements with a small letter designation referring to specific elements. When referring to the elements collectively or to a non-specific one or more of the elements, the small letter designation may be dropped. This emphasizes that according to common practice, the various features of the drawings may not be drawn to scale. Included in the drawings are the following figures:

FIG. 3 is a schematic diagram illustrating a sectional side view along line A-A in FIG. 2;

FIG. 4 is a schematic diagram illustrating a sectional side view along line B-B in FIG. 2;

DETAILED DESCRIPTION OF THE INVENTION

Figure 1:
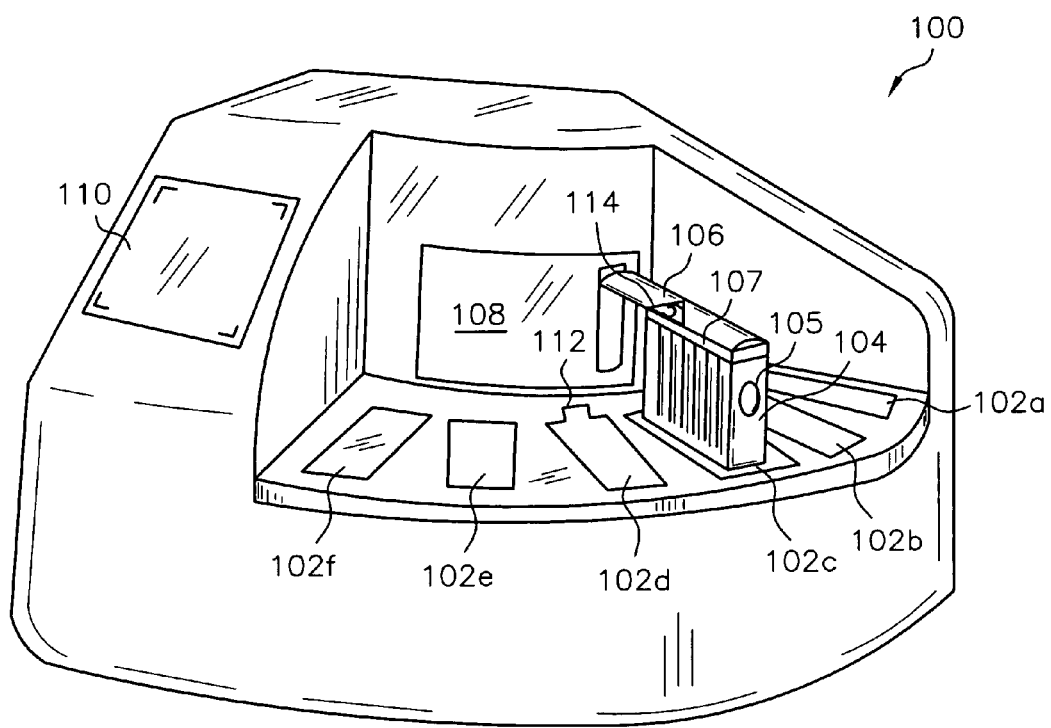
FIG. 1 is an illustration of a slide stainer in accordance with the present invention.

FIG. 1 depicts an automated slide stainer 100 for use in describing the present invention. The slide stainer 100 includes a plurality of stations for staining, rinsing, and/or drying one or more slides 104 containing one or more specimens (represented by specimen 105). In the illustrated embodiment, each station includes an aperture (represented by apertures 102a-f, e.g., six in the illustrated embodiment). One or more of the apertures may receive a vessel (described below). For example, four of the apertures, e.g., 102a-d, may receive vessels for staining the slides 104; one aperture, e.g., 102e, may receive a vessel for rinsing excess reagent from the slides 104 after staining; and one aperture, e.g., 102f, may contain drying apparatus for drying the slides 104 after staining and rinsing. The shape of the apertures may include a notch (represented by notch 112) or other feature for correctly orienting vessels within the apertures. Those skilled in the art will understand that the slide stainer 100 may contain essentially any number of apertures with some or all them being used for staining, rinsing, and/or drying. For example, the slide stainer may include a relatively larger number of apertures arranged in a grid pattern such as described in U.S. Pat. No. 5,573,727 to Keefe.

Figure 2:
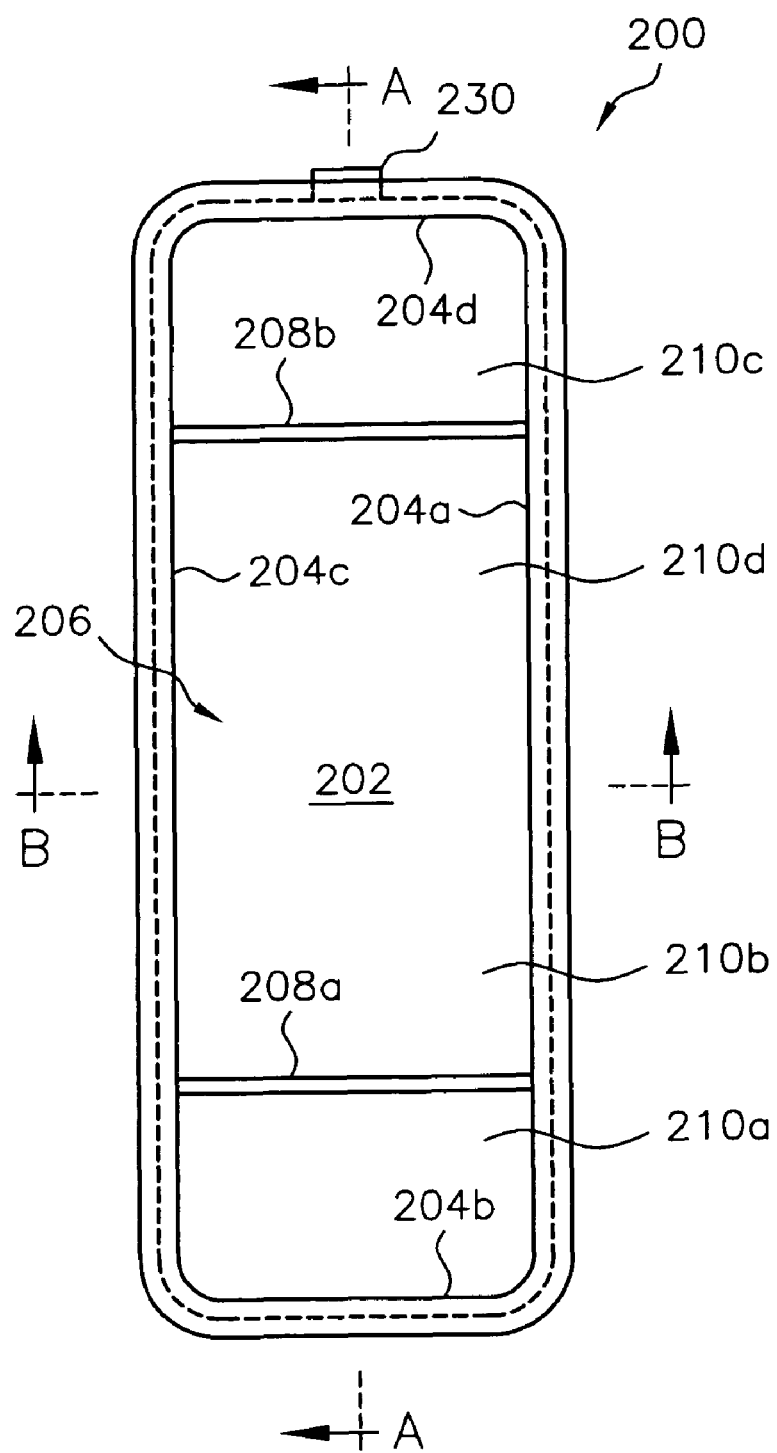
FIG. 2 is a schematic diagram illustrating a top view of an exemplary vessel for use in a slide stainer in accordance with the present invention.

FIG. 2 depicts a top view of an exemplary vessel 200 for use in a slide stainer (such as the slide stainer 100 in FIG. 1) in accordance with the present invention. FIG. 3 depicts a sectional view of the vessel 200 as depicted in FIG. 2 along line A-A and FIG. 4 depicts a sectional view of the vessel 200 as depicted in FIG. 2 along line B-B. In an exemplary embodiment, the vessel may be configured for placement within an aperture of a slide stainer.

The illustrated vessel 200 includes a bottom surface 202 and sidewalls (i.e., sidewalls 204a, 204b, 204c, and 204d) extending from the bottom surface 202 that define a cavity 206 having a volume for receiving fluid (such as reagents or water) for rinsing and/or staining slides positioned therein, e.g., dipped, dunked, deposited, etc. The vessel 200 further includes at least one partition (represented by a first partition 208a and a second partition 208b in the illustrated embodiment) that partitions the cavity 206 into two or more sub-cavities (represented by a first sub-cavity 210a, a second sub-cavity 210b, and a third sub-cavity 210c in the illustrated embodiment). Each sub-cavity has an associated volume that is less than the volume of the cavity 206. The partitions may be fixed in position within the vessel or may be moveable/removable.

The first partition 208a and the second partition 208b in the illustrated embodiment extend from the bottom surface 202 between a pair of opposed sidewalls (e.g., sidewalls 204a and 204c). In the illustrated embodiment, the partitions 208a and 208b are the same distance from sidewalls 204b and 204d, respectively. Accordingly, the volumes of sub-cavities 210a and 210c are the same. In an alternative embodiment, the first partition 208a and the second partition 208b may be different distances from sidewalls 204b and 204d, respectively, and, thus, would create cavities having different volumes and capable of receiving a different number of slides. Various other partition arrangements will be understood by those of skill in the art from the description herein.

Although illustrated with two partitions 208a and 208b, it will be understood by one of skill in the art from the description herein that there may be more or less partitions, which create more or less sub-cavities, without departing from the scope of the present invention. It will further be understood from the description herein that the dimensions and shape of the vessel 200 can vary widely without departing from the scope of the present invention. For example, the vessel 200 could be square, circular, or have essentially any geometric shape.

In an exemplary embodiment, the sidewalls 204 are substantially perpendicular to the bottom wall 202. In the illustrated embodiment, as best shown in FIGS. 3 and 4, the sidewalls 204a-d of the vessel 200 angle outward slightly (e.g., by approximately 3 degrees from perpendicular) to facilitate placement of the vessel 200 in an aperture of a slide stainer 100 (FIG. 1). Furthermore, a lip 302 extending from the sidewalls 204a-d along a top edge of the vessel 200 facilitates handling of the vessel 200 (e.g., carrying the vessel, inserting the vessel into the aperture, and removing the vessel from the aperture).

In an exemplary embodiment, the shape of the vessel may include a projection 230 or other feature for correctly orienting the vessel 200 within an aperture of a slide stainer. For example, the projection 230 of the vessel 200 may be configured for insertion within the notch 112 of aperture 102e in FIG. 1 such that there is only one correct orientation of the vessel within the aperture. In an alternative exemplary embodiment, the vessel does not include orienting features.

Figure 5:
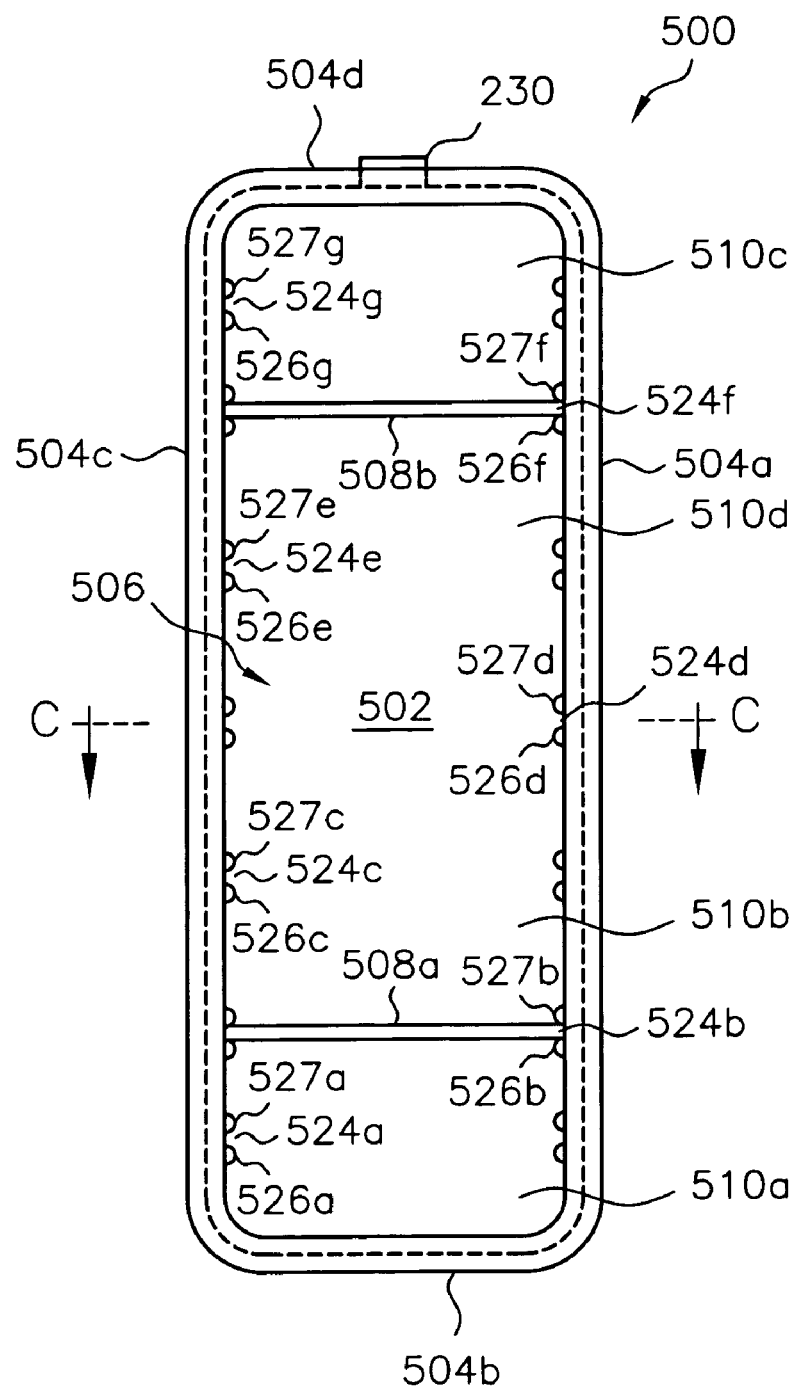
FIG. 5 is a schematic diagram illustrating a top view of an alternative exemplary vessel for use in a slide stainer in accordance with the present invention.
Figure 6:
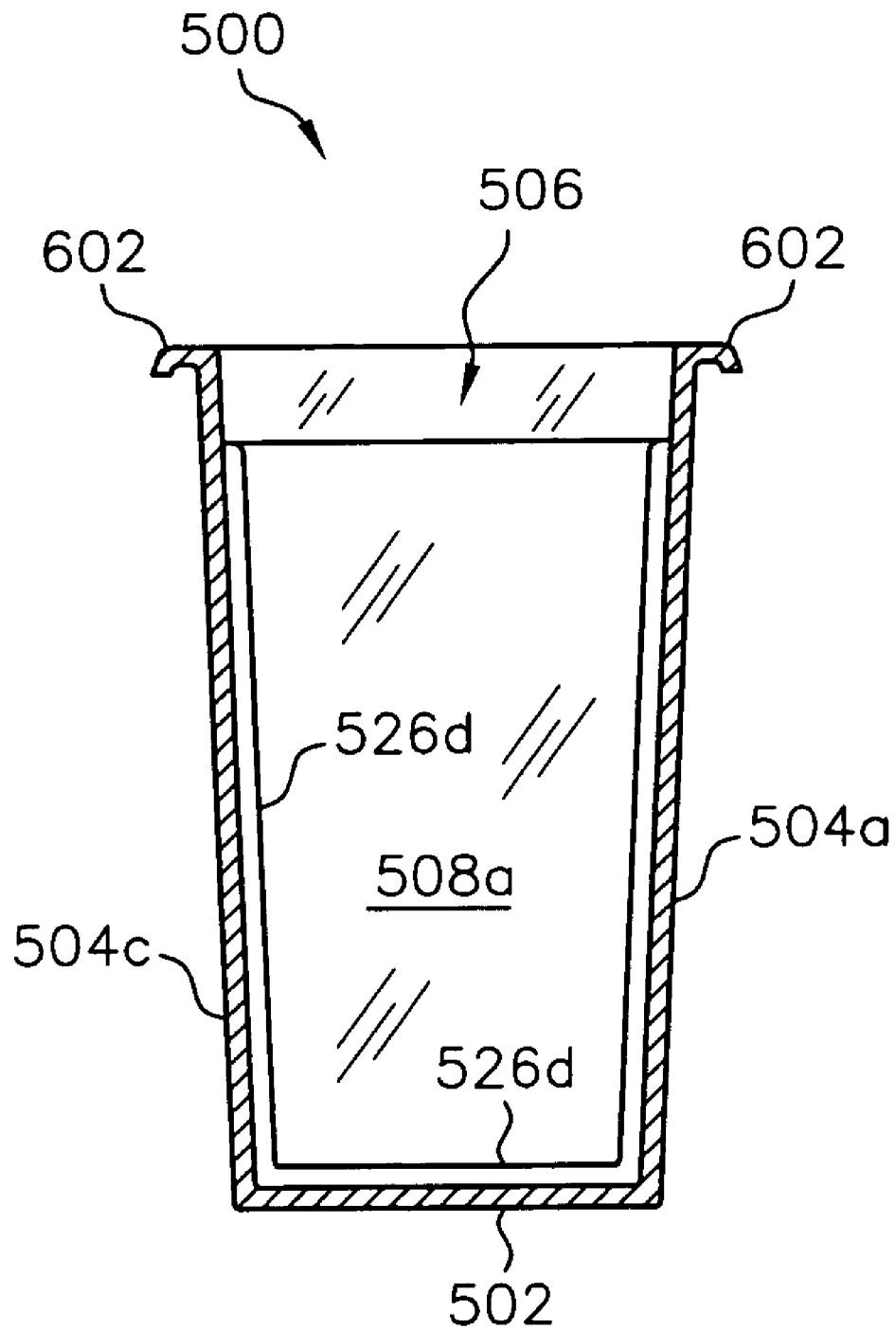
FIG. 6 is a schematic diagram illustrating a sectional side view taken along line C-C in FIG. 5.

FIG. 5 depicts a top view of an alternative exemplary vessel 500. FIG. 6 depicts a sectional view of the vessel 500 as depicted in FIG. 5 along line C-C. The illustrated vessel 500 includes a bottom surface 502 and sidewalls (i.e., sidewalls 504a, 504b, 504c, and 504d) extending from the bottom surface 502 that define a cavity 506 having a volume. A lip 602 extends from the sidewalls 504a-d along a top edge of the vessel 500. The vessel 500 may include orienting features similar to those described above with reference to vessel 200.

The illustrated vessel 500 includes a plurality of ridges (represented by ridges 526a-g and 527a-g). In an exemplary embodiment, the ridges are continuous. For example, ridge 526d extends down a first sidewall 504a, across the bottom surface 502, and up a second sidewall 504c opposite the first sidewall 504a. The ridges are attached to inner surfaces of the sidewalls 504a and 504c and the bottom surface 502. The ridges define slots (represented by slots 524a-g) for receiving one or more removable partitions (represented by removable partitions 508a and 508b). For example, ridges 526b and 527b define slot 524b for receiving removable partition 508a. In an exemplary embodiment, a fluid tight seal is created when a partition is inserted into a slot such that fluid on one side of the partition is prevented from flowing to the other side of the partition.

In an exemplary embodiment, as illustrated in FIG. 5, the removable partitions 508a and 508b are placed in slots 524b and 524f, respectively. Slot 524b is defined by ridges 526b, 527b, and slot 524f is defined by ridges 526f and 527f. The multiple slots 524a-g allow a user to change the number and size of sub-vessel cavities (e.g., vessel sub-cavities 510a-c) by selectively placing removable partitions (e.g., partitions 508a and 508b) into the desired slots. In the illustrated embodiment, the first removable partition 508a and the second removable partition 508b partition the cavity 506 into a first sub-cavity 510a, a second sub-cavity 510b, and a third sub-cavity 510c.

Figure 7:
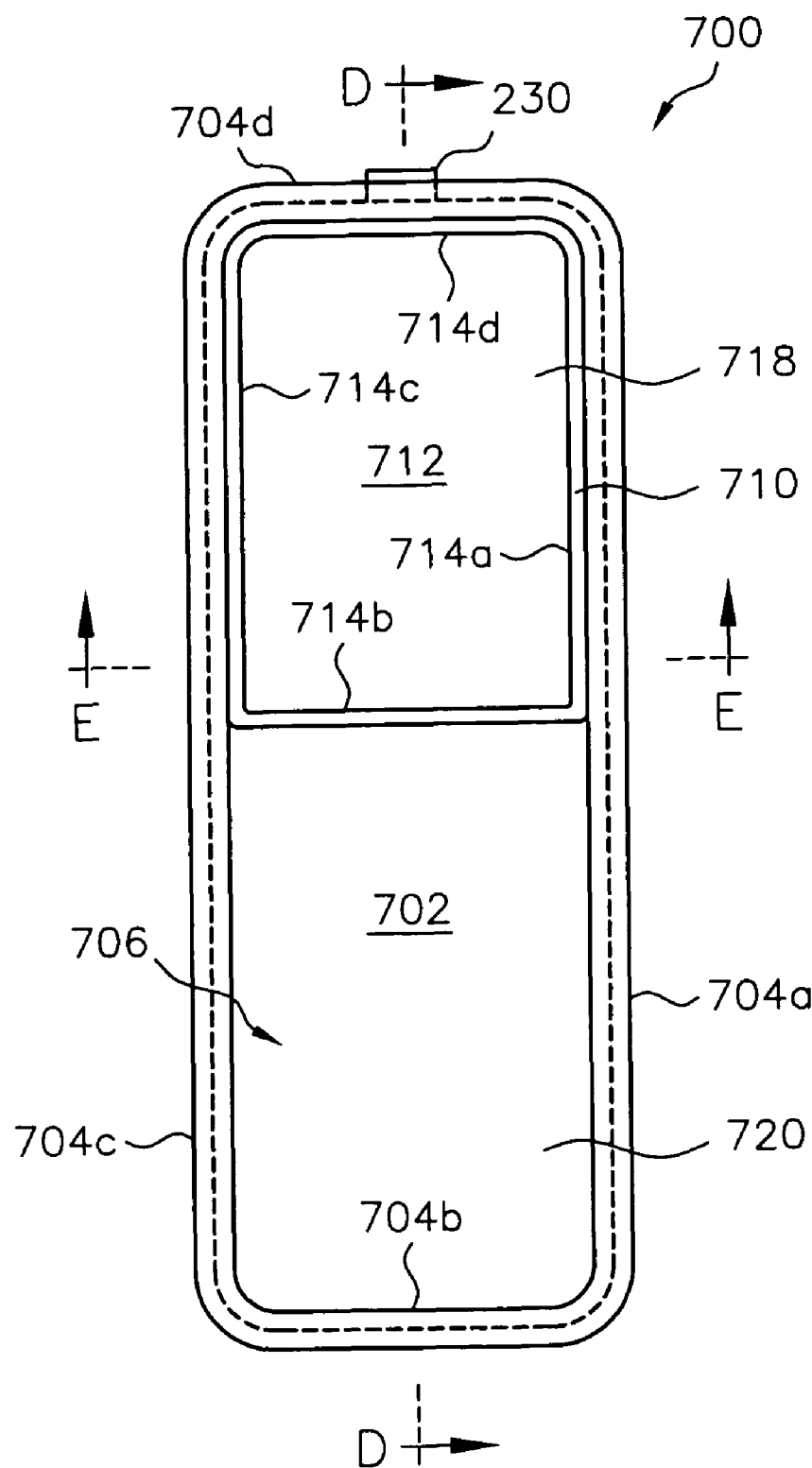
FIG. 7 is a schematic diagram illustrating a top view of another exemplary vessel for use in a slide stainer in accordance with the present invention.
Figure 9:
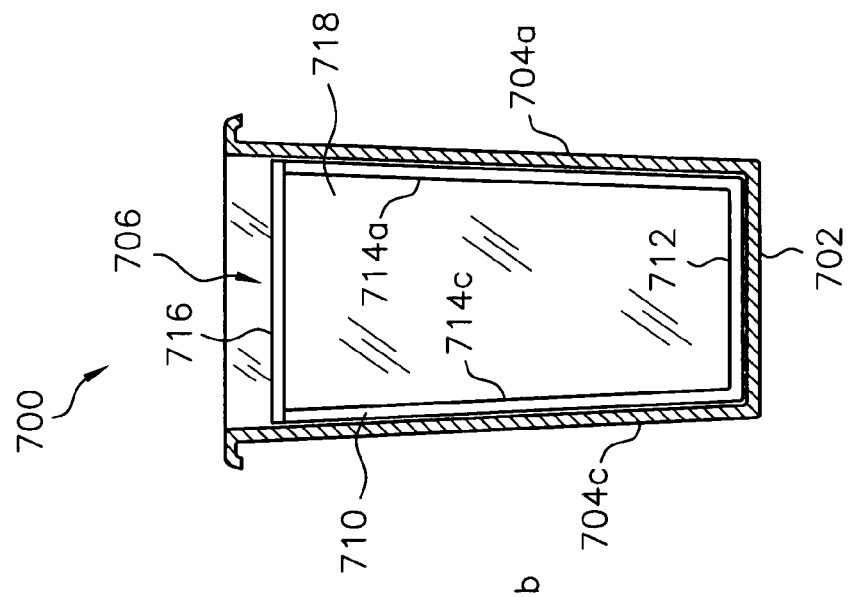
FIG. 9 is a schematic diagram illustrating a sectional side view along line E-E in FIG. 7.
Figure 8:
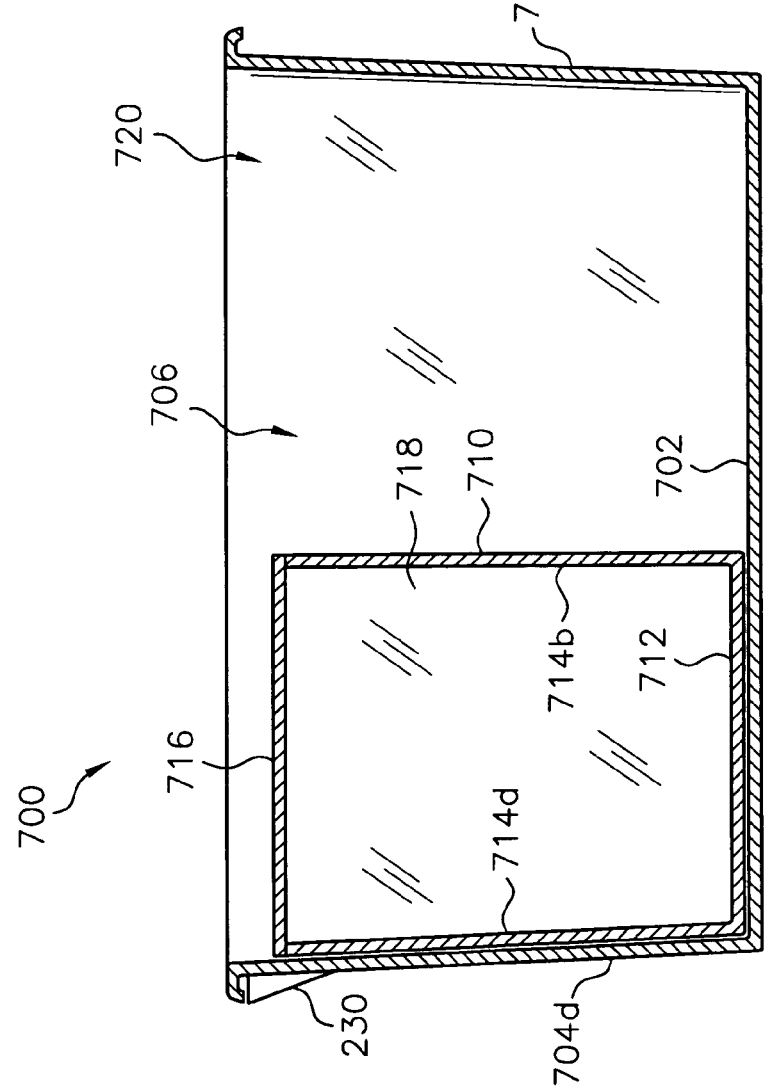
FIG. 8 is a schematic diagram illustrating a sectional side view along line D-D in FIG. 7.

FIG. 7 depicts a top view of an alternative exemplary vessel 700 for use in a slide stainer (such as the slide stainer 100 in FIG. 1) in accordance with the present invention. FIG. 8 depicts a sectional view of the vessel 700 as depicted in FIG. 7 along line D-D and FIG. 9 depicts a sectional view of the vessel 700 as depicted in FIG. 7 along line E-E. In an exemplary embodiment, the vessel may be configured for placement within an aperture of a slide stainer. The vessel 700 may include orienting features similar to those described above with reference to vessel 200.

The illustrated vessel 700 includes a bottom surface 702 and sidewalls (i.e., sidewalls 704a, 704b, 704c, and 704d) extending from the bottom surface 702 that define a cavity 706 having a volume for receiving fluid (such as reagents or water) for rinsing and/or staining slides dipped therein.

A removable block 710 is depicted within the illustrated vessel 700. The removable block 710 has a bottom surface 712 and side surfaces (i.e., side surfaces 714a, 714b, 714c, and 714d). Optionally, the removable block 710 may include a top surface 716. The bottom surface 712, side surfaces 714, and optional top surface 716 define an interior region 718. The interior region 718 may be hollow, partially filled, or completely filled. Suitable materials for use as the removable block will be understood by one of skill in the art from the description herein.

The removable block 710 may be held in position within the vessel, e.g., by its own weight, with fasteners (not shown) on the removable block 710 and/or one or more surfaces of the vessel 702, and/or by the shape of the removable block 710 with respect to the vessel 702. Other suitable methods for holding the removable block in position within the vessel 710 will be understood by one of skill in the art from the description herein. In an exemplary embodiment, the bottom surface 712 and two or more side surfaces 714 of the removable block 710 may contact the bottom surface 702 and corresponding side surfaces 704 of the vessel 700, respectively, to create a fluid tight seal when the removable block 710 is inserted into the vessel 710. In an alternative exemplary embodiment, a fluid tight seal may not be created.

The insertion of the removable block 710 within the vessel 700 creates a sub-cavity 720 within the cavity 706 of the vessel 700. Additionally, in embodiments where the removable block 718 is hollow and does not include a top surface 716, the removable block 710 creates another sub-cavity 722 within the cavity 706 of the vessel 700 that is defined by the bottom surface 712 and the side surfaces 714 of the removable block 718. Each sub-cavity has an associated volume that is less than the volume of the cavity 706.

In an exemplary embodiment, the sub-cavity 720 external to the removable block 710 is used for receiving fluids and slides for staining and/or rinsing the slides. In an alternative exemplary embodiment, the sub-cavity 722 within the removable block 710 is used for receiving fluids and slides for staining and/or rinsing the slides. In another alternative exemplary embodiment, the sub-cavity 720 and the sub-cavity 722 may both be used for receiving fluids and slides for staining and/or rinsing the slides.

Although a single removable block 710 is illustrated in the vessel, additional removable blocks (not show) may be added to the vessel to create more sub-cavities. In addition, the removable block 710 may be re-positioned to create additional sub-cavities. For example, if the removable block 710 were positioned midway between side surfaces 704b and 704d of the vessel 700 rather than against side surface 704d, an additional sub-cavity (not shown) would be created between the removable block 710 and side surface 704d. Various other arrangements of removable block(s) within the vessel 700 will be understood by one of skill in the art from the description herein.

In an exemplary embodiment, the vessels 200, 500, and 700 are dimensioned for insertion within an aperture of a slide stainer, e.g., aperture 102c of slide stainer 100 in FIG. 1. For example, if the aperture has a width of 1.75 inches, a length of 5.12 inches, and a depth of 3 inches, the vessels 200 and 500 may have the following dimensions: a maximum interior width of approximately 1.69 inches (as defined by the inside surfaces of sidewalls 204a/504a/704a and 204c/504c/704c), a maximum interior length of 5.06 inches (as defined by the inside surfaces of sidewalls 204b/504b/704b and 204d/504d/704d), and a maximum height of 2.94 inches (as defined by the bottom of the lip 302/602 and the bottom surface 202/502/702), assuming a wall thickness of 0.06 inches. Those of skill in the art will understand that the dimensions may vary substantially from the dimensions set forth above.

The vessel may have a vessel shape and the aperture may have a complementary shape that enables the vessel to be correctly positioned within the aperture in a limited number of predefined orientations, e.g., one orientation. For example, the vessel shape may include a projection 230 (FIG. 2) and the aperture may include a complementary notch 112 (FIG. 1) for receiving the projection. In another example, one side surface, e.g., side surface 204b, of a vessel 200 may be narrower than an opposed side surface, e.g., side surface 204d, such that the vessel has a wedge shape from a top view. Although the apertures are illustrates as separate distinct apertures, the apertures may be positions within one large aperture defined by the slide stainer with positioning structure (not shown) for maintaining the vessels in the correct position.

Referring back to FIG. 1, the slides 104 may be transported between the apertures 102a-f by a transport system. The illustrated transport system includes a transport arm 106 and a transport mechanism 108. The transport arm 106 is configured to accept a slide carrier 107 that supports up to a predetermined number of slides. In an exemplary embodiment, the predetermined number of slides corresponds to the maximum number of slides that may be simultaneous dipped into a non-partitioned vessel within an aperture while still providing adequate staining and/or rinsing of each slide. In an alternative exemplary embodiment, the predetermined number of slides is less than this maximum number, e.g., the total number of slides that may be simultaneously dipped into a sub-cavity of a partitioned vessel. Additionally, the slide carrier 107 may be configured to accept slides in a particular area only, such as in an area corresponding to a sub-cavity of a partitioned vessel positioned within an aperture. For example, the slide carrier 107 may be configured to accept no more than the total number of slides that may be simultaneously dipped into a sub-cavity in an area corresponding to the sub-cavity.

The slide carrier 107 may include indicia such as shape (e.g., triangle 114) or special shading/coloring (not shown) to indicate where slides should be placed if fewer than the maximum number of slides are to be used. For example, if only five slides are to be used in a slide carrier that supports forty slides, the slide carrier 107 may include a five (5) within the triangle 114 indicating where to position the five slides or a specially colored section that a slide stainer operator associates with correctly positioning five or fewer slides. Thus, damage to slides due to inadvertently positioning the slides in an area corresponding to a partition or side surface of a removable block may be prevented. Damage to slides may also be prevented through the use of slide carriers that only accept slides in an area corresponding to a sub-cavity.

The transport arm 106 is coupled to the transport mechanism 108, which is programmed based on instructions received from a processor (not shown) to position the transport arm 106 in a known manner. The transport mechanism 108 may be configured to move the transport arm 106 in a pattern such that the transport arm 106 is selectively positioned over each of the apertures 102e-f, and to lower and raise the transport arm 106 such that the slides 104 can be positioned within select ones of the apertures 102a-f (e.g., into partitioned vessels within the apertures).

Using a key pad 110, an operator of the slide stainer 100 programs the processor to configure the transport mechanism 108 such that the slides 104 supported by the transport arm 106 are selectively positioned within the plurality of apertures 102a-f (either in the aperture alone or in a vessel within an aperture) for a programmed amount of time in order to stain, rinse, and/or dry the slides 104. In addition, the processor may be programmed to agitate the slides 104 within one or more of the apertures 102a-f. Also, the processor may be programmed to control the flow of rinse fluid to the rinsing aperture 102e and to control the drying apparatus within the drying aperture 102f. Suitable transport system components, such as the transport arm 106, the transport mechanism 108, the processor, and the keypad 110, for use in the present invention will be readily apparent to those skilled in the art.

Figure 10:
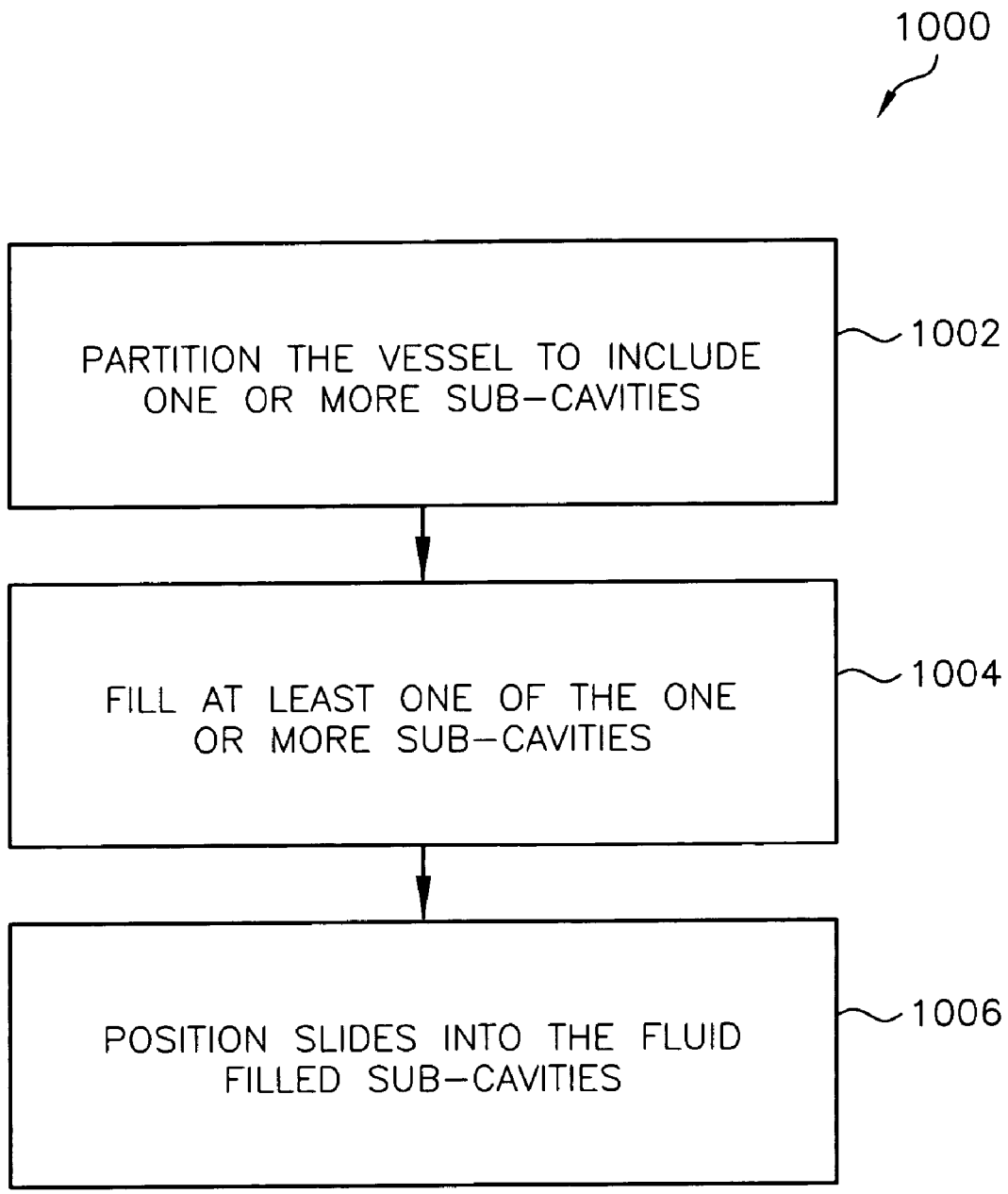
FIG. 10 is a flow chart of exemplary steps for applying fluid to a slide in accordance with the present invention.

FIG. 10 depicts a flow chart 1000 of exemplary steps for applying fluid to at least one slide. At block 1002, a vessel is partitioned to include one or more sub-cavities. In an exemplary embodiment, the vessel is partitioned when it is molded. In an alternative exemplary embodiment, the vessel is partitioned by inserting/removing removable partitions from the vessel. In another alternative exemplary embodiment, the vessel is partitioned by inserting/removing removable blocks from the vessel.

At block 1004, one or more of the sub-cavities are filled with fluid. In embodiments where removable blocks are used to create sub-cavities, a sub-cavity within the removable block and/or a sub-cavity within the vessel not occupied by the removable block may be filled with fluid.

At block 1006, the at least one slide is positioned into at least one of the one or more sub-cavities. In an exemplary embodiment, the slides are automatically positioned in the sub-cavities by an automated slide stainer such as automated slide stainer 100. In an alternative exemplary embodiment, the slides are manually positioned within the sub-cavities.

In use, the automated slide stainer 100 can be programmed by an operator to automatically position the slides within the vessel, e.g., to perform a staining procedure to stain, rinse, and/or dry slides. For example, assume that a staining procedure requires that two reagents be applied to the slides 104, that the slides 104 be rinsed to remove excess reagent, and that the slides 104 be dried. Further, assume that a first reagent aperture, e.g., aperture 102a, and a second reagent aperture, e.g., aperture 102b, contain vessels having cavities (or sub-cavities) filled with first and second reagents, respectively; that a rinsing aperture, e.g., aperture 102e, contains a rinsing vessel including a cavity (or sub-cavity) for rinsing the slides 104; and that a drying aperture, e.g., aperture 102f, contains drying apparatus for drying the slides 104. In this example, the processor is programmed via the keypad 110 to configure the transport mechanism 108 such that the control arm 106 sequentially positions the slides 104 within the first reagent aperture 102a for a first programmed amount of time, within the second reagent aperture 102b for a second programmed amount of time, within the rinsing aperture 102e for a third programmed amount of time to remove at least a portion of the first and second reagents, and within the drying aperture 102f for a fourth programmed amount of time. In addition, the processor may be programmed to control the amount of time rinse fluid is supplied to the rinsing aperture 102e and/or the flow rate of the rinse fluid. The processor may also be programmed to control the drying apparatus within the drying aperture 102f.

It will be understood by those skilled in the art that the slide stainer 100 can be programmed in an essentially infinite number of ways. For example, the slide stainer 100 can be programmed to position the slides 104 into any one or more of the apertures 102a-f in any order. In addition, the amount of time the slides 104 are positioned within each aperture 102a-f can be controlled. Rinse fluid and drying parameters can be controlled as well.

When a non-partitioned vessel in accordance with the prior art is used, the entire vessel is filled with reagent. Accordingly, the same amount of reagent is used regardless the number of slides being processed In an exemplary embodiment of the present invention, referring to FIGS. 2-4, where a partitioned vessel 200 in accordance with the present invention is used, the vessel 200 contains only one partition (e.g., partition 208a). The partition 208a creates two sub-cavities 210a and 210d (which is a combination of sub-cavities 210b and 210c resulting from the omission of partition 208b). For illustrative purposes only, assume sub-cavity 210a is configured to receive five slides. When only a small number of slides (e.g., one to five) needs processing, only sub-cavity 210a is filled with reagent. The amount of reagent needed to fill sub-cavity 210a is significantly less than the amount needed to fill a prior art vessel with no partitions. Therefore, the per-slide cost to process a small number of slides (e.g., one to five) is less than processing the same number of slides using a non-partitioned vessel.

In order to ensure the slides are placed in the proper position in relation to sub-cavity 210a, the slide carrier 107 may contain indicia indicating where to place the slides in the slide carrier or may be customized to accept slides only in an area corresponding to the sub-cavity 210a. Also, the vessel may contain indicia (not shown) indicating the number of slides capable of being processed in a sub-cavity thereof. In addition, the vessel 200 and apertures 102a-f (FIG. 1) may be configured such that they only fit together in one way/orientation (e.g., a wedge shape rather than a rectangular shape) or the vessel may include markings (not shown) corresponding to markings on the apertures 102a-f in order to assist an operator in properly aligning the vessel in the aperture.

In another exemplary embodiment, the vessel 200 is configured to have multiple partitions 208 that are fixed. The partitions could be configured such that each sub-cavity 210 has a different volume for accommodating a different number of slides. For example, with two partitions 208a and 208b, there are three sub-cavities (i.e., sub-cavities 210a, 210b, and 210c). For illustrative purposes only, assume sub-cavities 210a, 210b, and 210c are configured to accommodate five, ten, and twenty slides, respectively. If an operator is processing one through five slides, only sub-cavity 210a is filled with reagent. If an operator is processing six through ten slides, only sub-cavity 210b is filled with reagent. If an operator is processing eleven through fifteen sides, then sub-cavities 210a and 210b are filled with reagent. In this embodiment, the same vessel could accommodate anywhere from one to thirty-five slides. The same or different reagent may be used in each sub-cavity 210.

In another exemplary embodiment, referring to FIGS. 5 and 6, a vessel 500 has multiple slots 524 on sidewalls 504a and 504c and along a bottom surface 502. These slots 524 accommodate removable partitions 508a and 508b. A slide stainer operator may create sub-cavities that process a desired number of slides most efficiently. For example, if an operator needs to process eight slides, he or she places the removable partition 508 in the slot 524 that creates a sub-cavity that holds the least amount of reagent necessary to process that number of slides. Thus, less reagent is needed to fill the created sub-cavity than is needed to fill the entire cavity. Accordingly, the reagent is used more efficiently.

In another exemplary embodiment, referring to FIGS. 7, 8, and 9, a vessel 700 receives one or more removable blocks. A slide stainer operator may create sub-cavities that process a desired number of slides most efficiently. For example, if an operator needs to process eight slides, he or she places one or more removable blocks in the vessel 700 to create a sub-cavity that holds the least amount of reagent necessary to process that number of slides. Thus, less reagent is needed to fill the created sub-cavity than is needed to fill the entire cavity. Accordingly, the reagent is used more efficiently.

Having thus described a few particular embodiments of the invention, various alterations, modifications, and improvements will readily occur to those skilled in the art. For example, although the present invention is described with reference to automated slide stainers, it will be understood that the invention may also be applied to manual slide stainers. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

What is claimed is:

1. An apparatus for applying fluid to slides, the apparatus comprising:
   a vessel having a first sub-cavity for receiving a first plurality of slides, a second sub-cavity for receiving a second plurality of slides, and at least one removable partition defining in part the first and second sub-cavities, the first and second sub-cavities each configured to receive a fluid, wherein the at least one removable partition prevents fluid flow from the first and second sub-cavities;
   a slide carrier for receiving the first plurality of slides in a first area corresponding to the first sub-cavity and the second plurality of slides in a second area corresponding to the second sub-cavity; and
   a transport coupled to the slide carrier; and a processor coupled to the transport, the processor operable to move the transport such that the slide carrier is positioned over the vessel with the first area above the first sub-cavity and the second area above the second sub-cavity, the processor further operable to raise and lower the transport such that, when lowered, the first plurality of slides, when received by the slide carrier in the first area, is positioned at least partially within the first sub-cavity and the second plurality of slides, when received by the slide carrier in the second area, is positioned at least partially within the second sub-cavity.

2. The apparatus of claim 1, wherein the vessel includes; one or more removable blocks positioned within the vessel to create the first and second sub-cavities.

3. The apparatus of claim 2, wherein at least one of the one or more removable blocks has a hollow interior region and wherein the hollow interior region forms one of the first and second sub-cavities.

4. The apparatus of claim 2, wherein one or both of the first and second sub-cavities is created within the vessel in a region not occupied by the one or more removable blocks.

5. The apparatus of claim 1, wherein the vessel has a vessel shape and wherein the apparatus further comprises:
an aperture for receiving the vessel, the aperture having a complementary shape corresponding to the vessel shape that facilitates placement of the vessel within the aperture in a single predefined orientation.

6. An apparatus for applying fluid to slides, the apparatus comprising:
a vessel having a first sub-cavity for receiving a first plurality of slides, a second sub-cavity for receiving a second plurality of slides, and one or more integrally molded partitions defining in part the first and second sub-cavities, the first and second sub-cavities each configured to receive a fluid, wherein the one or more integrally molded partitions prevent fluid flow from the first and second sub-cavities;
a slide carrier for receiving the first plurality of slides in a first area corresponding to the first sub-cavity and the second plurality of slides in a second area corresponding to the second sub-cavity; and
a transport coupled to the slide carrier; and
a processor coupled to the transport, the processor operable to move the transport such that the slide carrier is positioned over the vessel with the first area above the first sub-cavity and the second area above the second sub-cavity, the processor further operable to raise and lower the transport such that, when lowered, the first plurality of slides, when received by the slide carrier in the first area, is positioned at least partially within the first sub-cavity and the second plurality of slides, when received by the slide carrier in the second area, is positioned at least partially within the second sub-cavity.

7. An apparatus for applying fluid to slides, the apparatus comprising:
a vessel having a first sub-cavity for receiving a first plurality of slides and a second sub-cavity for receiving a second plurality of slides, the first and second sub-cavities each configured to receive a fluid;
a slide carrier for receiving the first plurality of slides in a first area corresponding to the first sub-cavity and the second plurality of slides in a second area corresponding to the second sub-cavity, the slide carrier including indicia identifying the first area and the second area; and
a transport coupled to the slide carrier; and
a processor coupled to the transport, the processor operable to move the transport such that the slide carrier is positioned over the vessel with the first area above the first sub-cavity and the second area above the second sub-cavity, the processor further operable to raise and lower the transport such that, when lowered, the first plurality of slides, when received by the slide carrier in the first area, is positioned at least partially within the first sub-cavity and the second plurality of slides, when received by the slide carrier in the second area, is positioned at least partially within the second sub-cavity.

8. An apparatus for applying fluid to slides, the apparatus comprising:
a plurality of slide-staining stations, each of the plurality of slide-staining stations for receiving a plurality of slides;
a partitioned vessel having a cavity for receiving the plurality of slides, the partitioned vessel configured for insertion in one of the plurality of slide-staining stations and including a first sub-cavity and a second sub-cavity defined in part by a fixed partition within the cavity, the first sub-cavity for receiving a first fluid for staining a first sub-plurality of slides less than the plurality of slides and the second sub-cavity for receiving a second fluid for staining a second sub-plurality of slides less than the plurality of slides;
a slide carrier for receiving the plurality of slides, wherein the slide carrier receives the first sub-plurality of slides in a first area corresponding to the first sub-cavity and the second sub-plurality of slides in a second area corresponding to the second sub-cavity; and
a transport coupled to the slide carrier; and
a processor coupled to the transport, the processor operable to move the transport such that the slide carrier is positioned over the partitioned vessel with the first area above the first sub-cavity and the second area above the second sub-cavity, the processor further operable to raise and lower the transport such that the plurality of slides, when received by the slide carrier, is positioned at least partially within the cavity of the partitioned vessel, the first sub-plurality of slides, when received by the slide carrier in the first area, is positioned at least partially within the first sub-cavity of the partitioned vessel, and the second sub-plurality of slides, when received by the slide carrier in the second area, is positioned at least partially within the second sub-cavity of the partitioned vessel.

9. The apparatus of claim 8, wherein the first and second sub-cavities each have a respective volume and wherein the respective volumes of the first and second sub-cavities are different.

10. The apparatus of claim 8, wherein first and second fluids are different.

11. The apparatus of claim 8, wherein the slide carrier includes indicia identifying the areas corresponding to the first and second sub-cavities.

* * * * *